(12) United States Patent
Gündel

(10) Patent No.: US 8,111,884 B2
(45) Date of Patent: Feb. 7, 2012

(54) MEDICAL DIAGNOSTIC AND DATA PROCESSING SYSTEM

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 927 days.

(21) Appl. No.: 11/790,762

(22) Filed: Apr. 27, 2007

(65) Prior Publication Data

US 2007/0255121 A1  Nov. 1, 2007

(30) Foreign Application Priority Data

Apr. 28, 2006 (DE) .................... 10 2006 020 399

(51) Int. Cl.
*G06K 9/00* (2006.01)

(52) U.S. Cl. .................................. 382/128

(58) Field of Classification Search ........... 382/128–134
See application file for complete search history.

(56) References Cited

U.S. PATENT DOCUMENTS

| | | | | |
|---|---|---|---|---|
| 5,170,347 A * | 12/1992 | Tuy et al. | | 345/419 |
| 5,235,510 A | 8/1993 | Yamada et al. | | |
| 5,671,157 A * | 9/1997 | Saito | | 345/419 |
| 6,154,560 A * | 11/2000 | Cothren et al. | | 382/128 |
| 6,785,410 B2 * | 8/2004 | Vining et al. | | 382/128 |
| 6,829,379 B1 * | 12/2004 | Knoplioch et al. | | 382/131 |
| 7,206,462 B1 * | 4/2007 | Betke et al. | | 382/280 |
| 7,804,990 B2 * | 9/2010 | Kiraly et al. | | 382/128 |
| 2002/0065460 A1 * | 5/2002 | Murao | | 600/425 |
| 2003/0215119 A1 | 11/2003 | Uppaluri et al. | | |
| 2004/0078215 A1 | 4/2004 | Dahlin et al. | | |
| 2004/0078734 A1 | 4/2004 | Deuter | | |
| 2005/0110748 A1 | 5/2005 | Boeing et al. | | |
| 2005/0195190 A1 | 9/2005 | Williams et al. | | |
| 2006/0007188 A1 | 1/2006 | Reiner | | |
| 2006/0122467 A1 | 6/2006 | Harrington et al. | | |

FOREIGN PATENT DOCUMENTS

| | | |
|---|---|---|
| DE | 197 43 377 A1 | 3/1999 |
| DE | 102 10 145 A1 | 9/2003 |
| DE | 103 21 722 A1 | 12/2003 |
| DE | 102 54 941 A1 | 6/2004 |
| DE | 103 45 073 A1 | 5/2005 |
| DE | 10 2005 010 168 A1 | 10/2005 |
| WO | WO 03/046810 A1 | 6/2003 |
| WO | WO 2004/029851 A1 | 4/2004 |
| WO | WO 2006/017079 A2 | 2/2006 |

OTHER PUBLICATIONS

Ko, Jane P., u.a.: "CT Depiction of Regional Nodal Stations for Lung Cancer Staging". In: AJR 2000, vol. 174, 2000, American Roentgen Ray Society, S 775, 782.

* cited by examiner

*Primary Examiner* — Alex Liew

(74) *Attorney, Agent, or Firm* — Harness, Dickey & Pierce, P.L.C.

(57) ABSTRACT

A medical diagnostic and data processing system is disclosed. The system includes, in at least one embodiment, an arithmetic logic unit and an imaging diagnostic device that can be connected to the latter for data purposes, and a data memory in which data describing anatomical structures including lymph nodes are stored. The arithmetic logic unit is set up programmatically in such a way to produce an automatic assignment between a lymph node recorded by way of the imaging diagnostic device and data describing the lymph node that are stored in the data memory.

19 Claims, 3 Drawing Sheets

| N | R | L | E1 | E2 |
|---|---|---|---|---|
| | | | | |
| Uppermost mediastinal node | Cranial | Crossing of brachiocephalic vein and trachea | V1 | V2 |
| ... | ... | ... | ... | ... |
| Lower mediastinal node | Caudal | Bronchial branching | D1 | D2 |
| ... | ... | ... | ... | ... |

FIG. 3

| N | R | L | E1 | E2 |
|---|---|---|---|---|
|  |  |  |  |  |
| Uppermost mediastinal node | Cranial | Crossing of brachiocephalic vein and trachea | V1 | V2 |
| ... | ... | ... | ... | ... |
| Lower mediastinal node | Caudal | Bronchial branching | D1 | D2 |
| ... | ... | ... | ... | ... |

MEDICAL DIAGNOSTIC AND DATA PROCESSING SYSTEM

PRIORITY STATEMENT

The present application hereby claims priority under 35 U.S.C. §119 on German patent application number DE 10 2006 020 399.2 filed Apr. 28, 2006, the entire contents of which is hereby incorporated herein by reference.

FIELD

Embodiments of the invention generally relate to an apparatus and/or a method for processing diagnostic image data, for example to evaluate the shape of lymph nodes—in conjunction with a tumor diagnosis, for example.

BACKGROUND

Computed tomography methods for monitoring lymph nodes, such as are known in principle from the publication "CT Depiction of Regional Nodal Stations for Lung Cancer Staging" (Jane P. Ko et al., AJR 2000; 174, pages 775-782, American Roentgen Ray Society), for example, are suitable in tumor therapy.

For examinations in the mediastinum, that is to say in the middle part of the chest interior, consideration is also given in principle to the use of a mediastinoscopy known, for example, from DE 197 43 377 A1. A mediastinoscopy is carried out, as a rule, when pathological structures have previously been identified in an X-ray examination or computed tomography.

The observation of lymph node metastases is particularly important in the assessment of lung cancers. A widespread tumor stage classification is provided by the TNM classification defined by the UICC (International Union Against Cancer). A classification is performed in this case in terms of the clinically and, if appropriate, histopathologically determined anatomical extent of the tumor on the basis of a number of criteria: firstly, size and extent of the primary tumor are classified (parameter T). A further criterion for classifying the tumor is the absence or presence of regional lymph node metastases (parameter N).

Finally, the absence or presence of distant metastases features in the classification (parameter M). In the course of a tumor therapy, pictures are typically prepared at different points in time with the aid of an imaging diagnostic device, a classification using the TNM system being performed in each case. The aim of this is to monitor the response of the therapy to the primary tumor, and to monitor the lymph nodes and further metastases possibly affected. Diagnostic image data used for the classification can be suitable, in principle, for displaying anatomical structures in two- or three-dimensional views. In each case, the displays are to be carefully searched, it being possible to define anatomical orientation points (so-called landmarks) characteristic of the systemization of the search.

SUMMARY

In at least one embodiment, the invention expands the possibilities of evaluating diagnostic image data when investigating lymph nodes, in particular in conjunction with the diagnosis of tumors.

The medical diagnostic and data processing system of at least one embodiment operates with the aid of an imaging diagnostic device, preferably with the aid of a diagnostic device suitable for generating sectional images, in particular a computed tomography device. Combined sectional image methods can also be provided as are obtained, for example, by the PET/CT (Positron Emission Tomography/Computed Tomography) or SPECT/CT (Single Photon Emission Computed Tomography) combinations.

However, it is also possible in principle to use imaging devices based on other physical principles, for example magnetic resonance or ultrasound.

The diagnostic device is connected for data purposes to an arithmetic logic unit and to a data memory that can also be implemented in the form of a complex data processing network. Data describing anatomical structures including lymph nodes are stored in the data memory. These stored data can be reference data that are available for a comparison with a plurality of image data recorded in the examination of various patients. The reference data are not necessarily obtained with the aid of the imaging diagnostic device that is used as part of the medical diagnostic and data processing system.

In a departure therefrom, or in addition, it is also possible to store data that have been obtained in the examination of a specific patient, and are being held ready for a specific comparison with image data of the same patient acquired later. In each case, the arithmetic logic unit is set up programmatically in such a way that it is possible to produce an automatic assignment between a lymph node recorded by means of the imaging diagnostic device and data describing the lymph node that are stored, that is to say already put into memory at an earlier point in time in the data memory.

According to an advantageous refinement of at least one embodiment, designations of lymph nodes are stored in the data memory, and automatic assignment between such a designation and the corresponding, graphically displayable anatomical structure detected by way of the imaging diagnostic device being provided by way of the arithmetic logic unit. It is preferred here to work with a stored reference data record from which both geometric information relating to the relevant anatomical structures, and the designations of various lymph nodes can be extracted. When evaluating a picture prepared in the course of a tumor examination, in particular a picture imaging structures in the area of the chest, means for pattern recognition are used to identify a lymph node that can be recognized in the picture, and to assign it automatically to a specific lymph node of the reference data record.

The designation of a lymph node can preferably be displayed together with a two- or three-dimensional display that images at least one lymph node, the designation being inserted into a representation on a display screen in such a way that the assignment to the relevant lymph node is immediately visible. In the event of user-controlled marking of a recorded lymph node, for example by way of a mouse pointer, the designation of the lymph node is automatically inserted without further input manipulation in a user-friendly way. The functionality known in principle, for example, from DE 102 10 145 A1 (the entire contents of which are hereby incorporated herein by reference) as "tooltip" is thereby provided.

It is preferred to provide an automatic display of a selection list including a number of designations of lymph nodes in the case of an ambiguity between an anatomical structure recorded with the aid of the imaging diagnostic device and designations that come into question for lymph nodes. Even in the case in which there is no fully automatic unique assignment between a detected anatomical structure and one previously stored, there is a substantial simplification as against conventional systems in which medical image data are stored.

In accordance with an example refinement of at least one embodiment of the system, the user of the medical diagnostic and data processing system not only has the possibility of displaying an automatic assignment to an associated text starting from a pictorial display of an examined anatomical structure, but also, conversely, the possibility to select a corresponding graphic display by selecting a designation of a lymph node automatically. This eliminates a complicated manual search in a multiplicity of various displays, in particular sectional displays. If a number of displays exist in relation to a lymph node selected by text input, and these can also comprise stored reference displays, an appropriate selection is automatically offered.

If a lymph node is identified by way of the imaging diagnostic device, geometric properties of the lymph node are detected and stored, particularly in cases where a tumor invasion is being considered. It is preferred to undertake an automatic comparison between a geometric feature of a lymph node identified in an earlier picture and the corresponding feature of the lymph node identified in the current picture. This comparison forms a part of an automatically generated report.

Overall, the medical diagnostic and data processing system enables an automatic report of lymph nodes, particularly in the chest, but at the same time also, for example, in the area of abdomen, during the diagnosis of tumors by way of imaging methods.

BRIEF DESCRIPTION OF THE DRAWINGS

An example embodiment of the invention is explained in more detail below with the aid of drawings, in which, in a simplified illustration in each case:

FIG. 3 shows a detail of a table that can be stored in a data memory of the diagnostic and data processing system according to FIG. 1.

DETAILED DESCRIPTION OF THE EXAMPLE EMBODIMENTS

Figure 1:
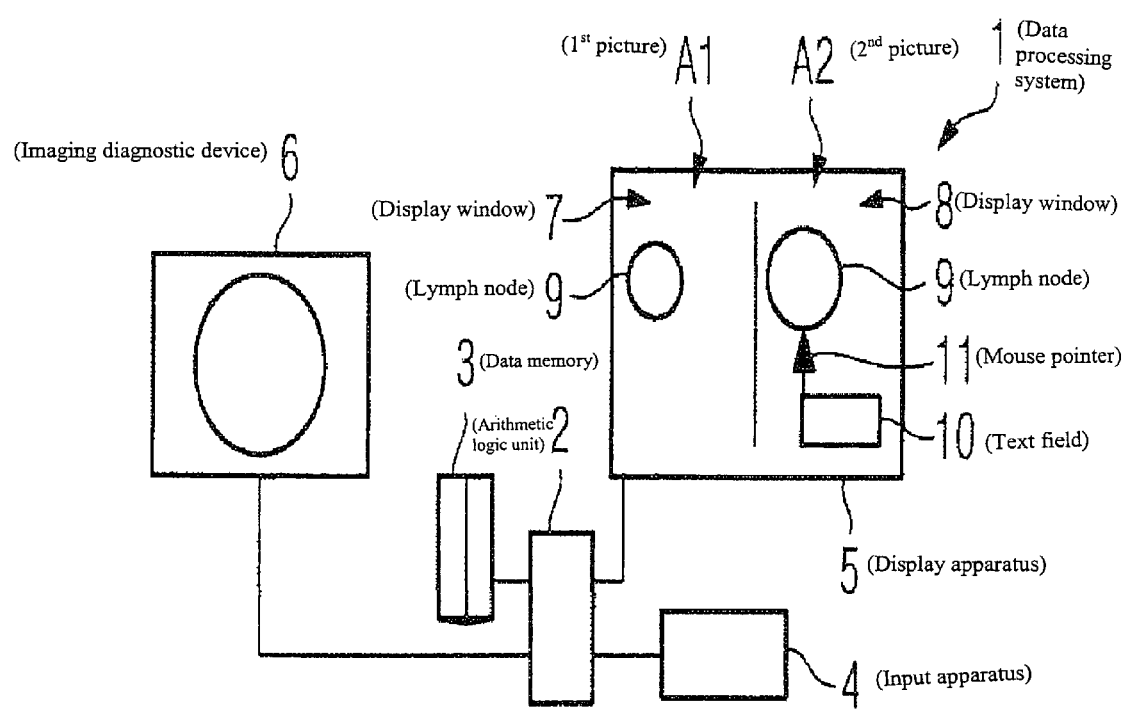
FIG. 1 shows a medical diagnostic and data processing system for computer-aided detection and classification of lymph nodes in conjunction with the diagnosis of tumors.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

A medical diagnostic and data processing system 1 illustrated in symbolic fashion in FIG. 1 includes an arithmetic logic unit 2, a data memory 3, an input apparatus 4, for example a keyboard and/or a mouse, a display screen as display apparatus 5, and an imaging diagnostic device 6, in particular a computed tomography device.

The diagnostic device 6 serves for preparing tomograms in the area of the chest, and enables both lung cancers to be detected, and the detection of lymph nodes that can be enlarged as a consequence of metastasizing. A patient is examined with the aid of the diagnostic device 6 at various points in time before, during and after a tumor therapy. Data recorded thereby are archived in various, intercorrelated data records in the data memory 3. In a departure from the simplified display according to FIG. 1, the data memory 3 can, just as in the case of the arithmetic logic unit 2, be a part of a complex data processing network for example inside a radiology information system (RIS) and/or a PACS system (Picture Archiving and Communication System).

Tomograms, or three-dimensional pictures, obtained at various points in time can optionally be displayed on the display screen 5, it also being possible in the example embodiment according to FIG. 1 to display two representations simultaneously in one display window 7 or 8 each. Here, a lymph node 9 is visible, in the way it was recorded at a first point in time, in a first picture A1 in the first display window 7 (on the left in FIG. 1), while the same lymph node 9 can be detected in a second picture A2, prepared at a later time, in the second display window 8. None of the anatomical structures surrounding the lymph node 9 are illustrated in the symbolic view according to FIG. 1.

In addition to the lymph nodes 9 enlarged by comparison with the older representation reproduced in the left-hand display window 7, a text field 10 pointing to the lymph node 9 is visible in the right-hand display window 8. Said field appears automatically for the purpose of tooltip functionality when the user employs an input apparatus 4 to place a mouse pointer 11 on the display screen 5 in the region of the lymph node 9. The designation of the lymph node 9 is reproduced in plain text in the text field 10 (not to be seen in FIG. 1).

Figure 2:
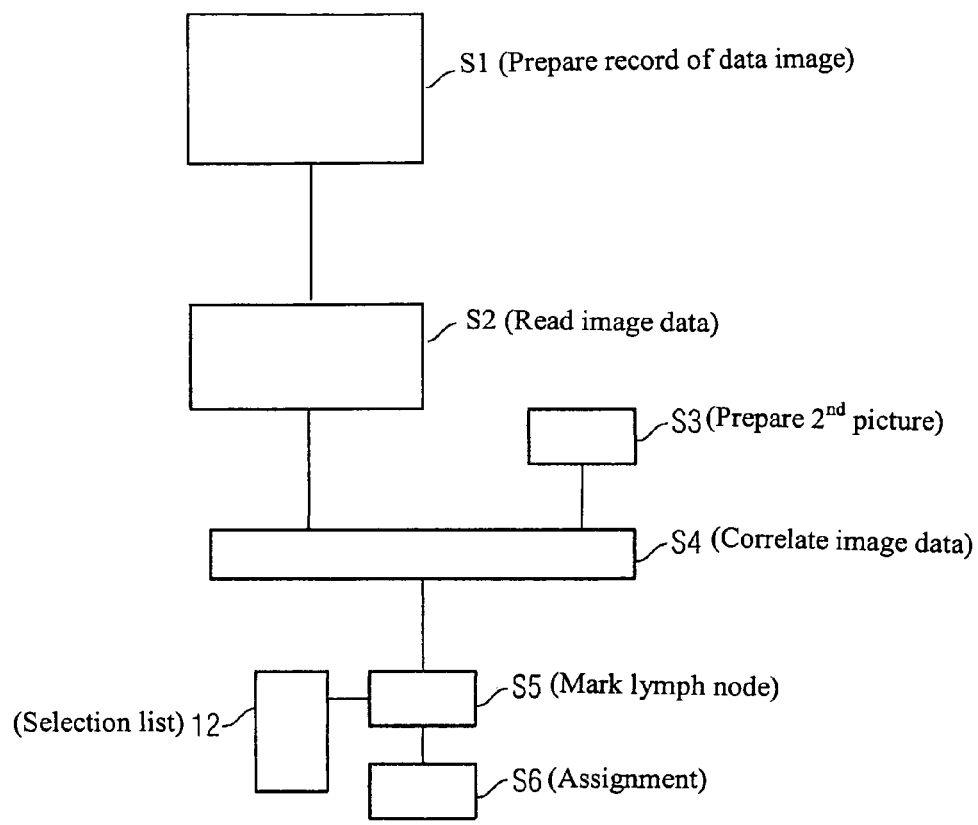
FIG. 2 shows a flowchart of a method for processing diagnostic image data that is to be carried out with the aid of the diagnostic and data processing system according to FIG. 1.

The lymph node 9 is identified automatically with the aid of geometric features of the anatomical structures in the area of the chest that are detected in picture A2, but not reproduced, except for the lymph node 9 in FIG. 2. It is preferred to segment three-dimensional image data obtained with the aid of the diagnostic device 6, in order to determine organs and organ parts inside the examined volume. The methods known under the designation of "Region Growing" or "Random Walker", for example, are suitable for the segmentation. A VRT (Volume Rendering Technique) method for 3D-visualization is described in DE 103 45 073 A1. Reference is also made to DE 10 2005 010 168 A1 with reference to multislice data conversion rates (MPR).

If lymph nodes 9 are identified within a two-dimensional or three-dimensional picture A1, A2, they can be highlighted automatically or graphically under user control. It is possible in this case, for example, to set parameters of a program used to operate the arithmetic logic unit 2 in such a way that in the event of user-controlled marking of the lymph node 9 in the first picture A1, the same lymph node is automatically marked in the same way in the second picture A2. This enables a very fast first comparison between the shape and size of the lymph node 9 at the point in time of preparation of the first picture A1 and the corresponding geometric properties of the lymph node 9 at the point in time of preparing the second picture A2. At the same time, the link is produced to data relating to the lymph node 9 and stored in the data memory 3 and which, for example, additionally comprise anatomical information.

The temporal sequence of various steps undertaken with the aid of the medical diagnostic and data processing system 1 is explained below with the aid of the flowchart illustrated in FIG. 2:

In a first step S1, the imaging diagnostic device 6 prepares a record of two- or three-dimensional image data of the area to be examined. In a second step S2, the image data organized in pixel form (2-D data) or voxel form (3-D data) are read into the data memory 3, and are available later on as background data for use by way of the arithmetic logic unit 2. Independently of whether the stored data that can be displayed in the form of the first picture A1 are present as 2-D or 3-D data, it is possible to extract from them information relating to at least one, preferably a number of lymph nodes 9 in the area examined. In addition, it is preferred to provide in the data memory 3 further data relating to the anatomical structures in the area examined, for example data based on earlier comparative examinations.

At a later point in time, after termination of steps S1, S2, the second picture A2 is prepared in a third step S3 by way of the imaging diagnostic device 6. The period of time between the termination of the second step S2 and the carrying out of the third step S3 is of no fundamental importance for the sequence of the further method. In any case, in the following step S4 the more recent data, recorded in the third step S3 and including information relating to at least one lymph node 9, are correlated with the information already stored in the second step S2 and relating to the same anatomical structures.

Various functionalities are available as a result of this correlation undertaken by way of the arithmetic logic unit 2, as explained below with the aid of the further steps S5, S6: for example, as already mentioned in conjunction with FIG. 1, it is possible in the fifth step S5 to mark a lymph node 9 in a picture A1, A2. If, thereupon, the designation of this lymph node 9 cannot be determined directly on the basis of anatomical features, the display device 5 is used to display a selection list 12 that includes all the lymph nodes 9 coming into consideration, the number of the various lymph nodes 9 set forth in the selection list 12 being less than the number of the lymph nodes 9 present in the volume examined and capable of being detected with the aid of the imaging diagnostic device 6.

After the unique identification, carried out in a fully automatic or partly automatic fashion, of a specific lymph node 9, the latter is assigned geometric features as described in more detail below with the aid of FIG. 3. This assignment is also preferably performed in a fully or at least partially automated fashion. Consequently, in order to determine the relevant variables, for example to measure a volume of the lymph node 9, use is preferably made of an image evaluation software suitable for the purpose. However, it is likewise also possible in principle to extract the relevant variables from the picture A1, A2 visible on the display screen 5 with the aid of simple software tools that include, for example, linear scales that can be inserted into a graphic. The data determined are assigned in each case to the remaining, already stored data relating to the lymph node 9 such that the temporal development of individual variables, in particular the extent of the lymph node 9 can be traced and displayed in a targeted manner.

The sixth step S6 following the step S5 in the simplified scheme according to FIG. 2 can be carried out without any defined temporal connection with step S5, that is to say at any desired point in time after termination of step S4. In step S6, an assignment is likewise undertaken between a lymph node 9 and its designation as well as, if appropriate, additional stored data but, by contrast to step S5, starting from the explicit designation. This yields an assignment to pictures A1, A2 that display the lymph node 9. If, as in the preceding case, a number of pictures A1, A2 exist that display the selected lymph node 9, it is possible to display a selection list 12 in a way similar to the case of step S5. The sequence of the pictures A1, A2 set forth on this selection list 12 can be determined by way of settable criteria for example the point in time of the respective examination.

A detail of a data record stored in the data memory 3 and relating to different lymph nodes 9 is reproduced in tabular form in FIG. 3. The designation of various lymph nodes 9 is specified in the column denoted by N (name). The columns R and L specify the direction and location, respectively, of the corresponding lymph node 9. The directional specification "cranial" stands, for example, for "lying toward the head", while the directional specification "caudal" stands for "lying downward". In total, the lymph nodes 9 in the chest are assigned fourteen so-called stations, there existing, as a rule, per station a number of lymph nodes 9 characterized by different directional and positional data R, L.

Each lymph node 9 that is detected in the course of the examinations carried out with the aid of the imaging diagnostic device 6 is, in addition to the information already stored before the beginning of the first examination, in particular included in columns N, R, L, is assigned further entries E1, E2 as soon as the corresponding information is determined by evaluating the pictures A1, A2.

In the example according to FIG. 3, column E1 includes entries that have been determined during the evaluation of the first picture A1, while column E2 includes entries not determined until the evaluation of the second picture A2. Volume data V1, V2 and diameter data D1, D2 that describe the respective lymph node 9 are respectively entered in the two columns E1, E2. As explained with the aid of FIGS. 1 and 2, these data D1, D2, V1, V2 obtained at various points in time are input in largely automated fashion.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical diagnostic and data processing system, comprising:
    an arithmetic logic unit;
    an imaging diagnostic device, connectable to the arithmetic logic unit;
    a data memory to store data describing anatomical structures including lymph nodes, the arithmetic logic unit being set up programmatically to produce an automatic assignment between a lymph node recorded via the imaging diagnostic device and data describing the lymph node stored in the data memory; and
    a display device configured to automatically display a selection list including a number of designations of lymph nodes is provided in the case of an ambiguity between an anatomical structure recorded with the aid of the imaging diagnostic device and designations of lymph nodes, wherein
        the arithmetic logic unit is configured such that, in the event of user-controlled marking of a lymph node, an associated designation is inserted automatically and the associated designation is a name of the lymph node.

2. The medical diagnostic and data processing system as claimed in claim 1, wherein the imaging diagnostic device is designed as a device suitable for generating sectional images.

3. The medical diagnostic and data processing system as claimed in claim 2, wherein the imaging diagnostic device is a computer tomograph.

4. The medical diagnostic and data processing system as claimed in claim 1, wherein designations of lymph nodes are stored in the data memory, and automatic assignment between such a designation and the corresponding, graphically displayable anatomical structure is provided by the arithmetic logic unit.

5. The medical diagnostic and data processing system as claimed in claim 4, wherein the arithmetic logic unit is set up programmatically in such a way that a representation of the lymph node with insertion of the associated designation is displayable by a display apparatus.

6. The medical diagnostic and data processing system as claimed in claim 5, wherein the arithmetic logic unit is set up programmatically such that, in the event of inputting of a designation of a lymph node, a corresponding graphic display is automatically selected.

7. A method for processing diagnostic image data, comprising:
    preparing, using an imaging diagnostic device, a first picture of a tissue in which at least one lymph node is located;
    storing the first picture in a data memory;
    preparing a second picture, via the imaging diagnostic device, at a later point in time; and
    automatically making an assignment between a lymph node identified in the second picture and the corresponding lymph node in the first picture, wherein
    in the event of a user-controlled marking of the lymph node, an associated designation is inserted automatically and the associated designation is a name of the lymph node, and
    an automatic display of a selection list including a number of designations of lymph nodes is provided in the case of an ambiguity between an anatomical structure recorded with the aid of the imaging diagnostic device and designations of lymph nodes.

8. The method as claimed in claim 7, wherein the diagnostic image data include a picture of at least one lymph node in the chest obtained with the aid of the imaging diagnostic device.

9. The method as claimed in claim 7, wherein the diagnostic image data include a picture of at least one lymph node in the abdomen obtained with the aid of the imaging diagnostic device.

10. The method as claimed in claim 7, wherein an automatic comparison is undertaken between a geometric feature of a lymph node identified in the first picture and the corresponding feature of the lymph node identified in the second picture.

11. The medical diagnostic and data processing system as claimed in claim 2, wherein designations of lymph nodes are stored in the data memory, and automatic assignment between such a designation and the corresponding, graphically displayable anatomical structure is provided by the arithmetic logic unit.

12. The medical diagnostic and data processing system as claimed in claim 3, wherein designations of lymph nodes are stored in the data memory, and automatic assignment between such a designation and the corresponding, graphically displayable anatomical structure is provided by the arithmetic logic unit.

13. The method as claimed in claim 8, wherein the diagnostic image data include a picture of at least one lymph node in the abdomen obtained with the aid of the imaging diagnostic device.

14. The method as claimed in claim 8, wherein an automatic comparison is undertaken between a geometric feature of a lymph node identified in the first picture and the corresponding feature of the lymph node identified in the second picture.

15. The method as claimed in claim 9, wherein an automatic comparison is undertaken between a geometric feature of a lymph node identified in the first picture and the corresponding feature of the lymph node identified in the second picture.

16. A system for processing diagnostic image data, comprising:

means for preparing a first picture of a tissue in which at least one lymph node is located and for preparing a second picture at a later point in time;

means for storing the first picture in a data memory;

means for automatically making an assignment between a lymph node identified in the second picture and the corresponding lymph node in the first picture: and means for automatically displaying a selection list including a number of designations of lymph nodes is provided in the case of an ambiguity between an anatomical structure recorded with the aid of the imaging diagnostic device and designations of lymph nodes, wherein the means for automatically making the assignment is configured such that, in the event of a user-controlled marking of the lymph node, an associated designation is inserted automatically and the associated designation is a name of the lymph node.

17. A computer readable medium including program segments for, when executed on a computer device, causing the computer device to implement the method of claim 7.

18. The medical diagnostic and data processing system of claim 1, wherein the name of the lymph node is based on a location of the lymph node.

19. The method of claim 7, wherein the name of the lymph node is based on a location of the lymph node.

* * * * *